Figure 1:
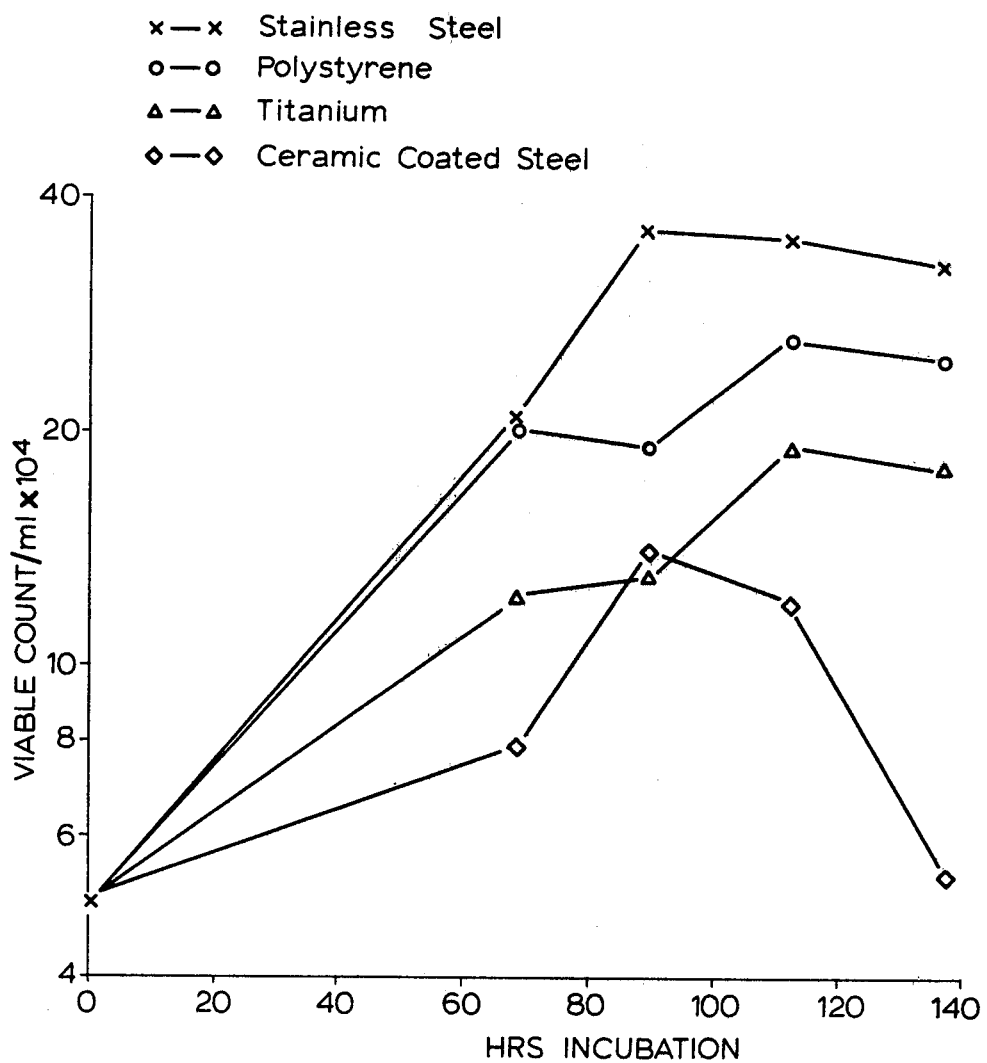

United States Patent [19]

Birch et al.

[11] 4,343,904

[45] Aug. 10, 1982

[54] PROCESS AND APPARATUS FOR GROWING ANIMAL CELLS

[75] Inventors: John R. Birch, High Wycombe; Terence Cartwright, Benson; John A. Ford, Wallingford, all of England

[73] Assignee: G. D. Searle & Co., Skokie, Ill.

[21] Appl. No.: 180,063

[22] Filed: Aug. 21, 1980

[30] Foreign Application Priority Data

Aug. 24, 1979 [GB] United Kingdom ............. 7929567

[51] Int. Cl.³ .................. C12N 5/00; C12M 1/14; C12M 1/06
[52] U.S. Cl. .................. 435/240; 435/285; 435/310; 435/313; 435/315
[58] Field of Search ............ 435/284, 285, 310, 240, 435/241, 313, 315

[56] References Cited

U.S. PATENT DOCUMENTS

| | | | |
|---|---|---|---|
| 3,407,120 | 10/1968 | Weiss et al. | 435/285 |
| 3,905,865 | 9/1975 | McAleer et al. | 435/285 |
| 3,933,585 | 1/1976 | McAleer et al. | 435/284 |
| 4,208,483 | 6/1980 | Lee | 435/284 |
| 4,262,090 | 4/1981 | Colby et al. | 435/240 |

*Primary Examiner*—David M. Naff
*Assistant Examiner*—Kathleen S. McCowin
*Attorney, Agent, or Firm*—Albert Tockman; James G. Passé

[57] ABSTRACT

Animal cells are grown in a vertically disposed cylindrical vessel containing a stack of parallel spaced-apart discs inclined at least 5° from the horizontal and mounted to a rotatable axial shaft. The vessel is closed by a top plate having a plurality of inlets and a bottom plate with an outlet, and contains an external pumping loop for circulating contents of the vessel from the bottom to the top of the vessel. Growing of the cells is carried out by substantially filling the vessel with a mixture of animal cells and growth medium, allowing the cells to settle on the disc surfaces and then rotating the axial shaft at a speed of at least 5 rpm while continuously circulating the vessel contents from the bottom to the top of the vessel. This process and apparatus provides efficient mixing and ensures a homogeneous system within the vessel.

3 Claims, 3 Drawing Figures

PROCESS AND APPARATUS FOR GROWING ANIMAL CELLS

This invention relates to a stack plate culture; more particularly, it relates to a process for growing animal cells and the production of metabolites therefrom, also to an apparatus for use in the process.

Currently, the growing of animal cells on a large scale is carried out in apparatus comprising a vessel for the growth medium and arranged within the vessel a plurality of surfaces upon which the cells grow, these surfaces being discs or plates spaced apart from one another.

British Patent No. 1,097,669 describes a tissue culture propagator comprising a vessel for the growth medium and a series of spaced-apart plates arranged as a stack on a rack within the vessel. The stack of plates remains stationary within the vessel and the necessary circulation of the growth medium within the vessel is achieved by means of an air lift pump. In use, the vessel is filled to the required degree with growth medium inoculated with the cells it is desired to grow which are allowed to settle on the surface of the plates and the required circulation within the vessel is produced by an air lift pump or by magnetic or vibratory agitation.

A modified apparatus of this type has been proposed by Biotec AB, of Sweden which apparatus comprises a stack of discs mounted on a rotatable axial shaft within a cylindrical vessel. In use, this apparatus is first positioned vertically, i.e. with the axial shaft at right angles to the working surface, the vessel is filled with nutrient medium, cells are plated onto the disc surfaces and then the apparatus is placed in a horizontal position, about half of the nutrient medium is removed from the vessel and the shaft and stack of discs rotated so that only the lower section of the discs are at any one time passing through growth medium lying in the vessel.

In British Pat. No. 1,393,654, a further modification of the Biotec apparatus is proposed in which the ratio of disc diameter to internal vessel diameter is from 0.80:1 to 0.90:1 and in addition it is preferred that the distance between the edge of the discs and the internal wall of the vessel is from ½ to ¾ of an inch (from 1.27 to 1.905 cm). It is also preferred that the ratio of total surface area of the discs to the volume of the vessel is from 5.5:1 to 6.0:1. In view of the nature of the operation of this apparatus, and of the Biotec apparatus, rotation of the shaft needs to be slow to minimise the shear forces produced on the cells as the discs rotate in and out of the growth medium. Rotation speeds of the order of 0.5 rpm have been suggested as a practical maximum for this apparatus. Lower speeds are frequently used.

The types of apparatus described above, although effective for cell growth, have various disadvantages resulting from features of design and operation, which make adequately controlled manipulation of the cellular synthetic process impossible for the production of useful cell metabolites. Thus, the use of a fixed stack of plates held in a notched rack results in complicated assembly, cleaning of the apparatus and harvesting of cells.

Circulation of the growth medium using an air lift pump cannot be efficiently performed without unacceptable foaming of the medium which may necessitate the addition of anti-foam agents which may adversely influence the growth and metabolism of tissue culture cells.

In the rotary type of apparatus described, the need to move the apparatus from the vertical to the horizontal is a real disadvantage when large scale apparatus is considered. The necessary slow rotational speeds makes the mixing in of subsequently added growth medium constituents and other reagents inefficient and also continuous measurement of conditions within the vessel cannot be made reliable, because poor mixing dictates that the vessel contents cannot function as a homogeneous system.

It has now been found that all of these disadvantages may be overcome by conducting the growth process in an apparatus comprising a vertically arranged vessel substantially filled with a mixture of growth medium and cells and containing a stack of parallel, spaced-apart metal plates fixedly mounted with respect to an axial shaft capable of relatively high rotational speeds, and providing means for circulation of the medium within the vessel from the bottom of the top of the vessel.

Accordingly, the present invention provides a process for growing animal cells by incubation with growth medium in a multi-plate growth apparatus which comprises substantially filling a vertically disposed cylindrical vessel with a mixture of cells and growth medium, which vessel is closed by top and bottom plates, the top plate being provided with a plurality of inlets and the bottom plate with an outlet, and the vessel is provided with a series of spaced apart parallel discs fixedly mounted with respect to a rotatable axial shaft within the vessel, allowing the cells to settle on the disc surfaces while maintaining the vessel contents at an optimum growth temperature and while infusing the vessel contents with a mixture of oxygen and carbon dioxide and thereafter rotating the axial shaft at a speed such as to produce a minimum plate tip velocity of 200 cm/min. for a period of time to allow optimum growth to occur and circulating the growth medium from the bottom to the top of the vessel by external pumping means.

In a typical 5 liter vessel, the rate of axial shaft rotation to achieve a plate tip velocity of 200 cm/min. will be of the order of 5 rpm.

In prior art processes, various materials have been proposed for the cell growth substrate. It has now been found that the ideal material for use as the plates of the apparatus according to the present invention is smooth stainless steel, which gives faster growth rates and higher maximum population densities than other conventional materials. FIG. 1 of the accompanying drawings illustrates growth curves of human diploid fibroblasts 17/1 growing in conventional RPMI 1640 culture medium + 10% serum. It has previously been proposed (U.S. Pat. No. 3,976,547) to use various metals, including stainless steel, as a cell growth substrate, but to so modify the surface of the material that it has irregularities greater in size than the diameter of the cells to be grown. No advantage has been found in such change in surface topography and in accordance with the present invention smooth plates are used.

The fact that the discs in the apparatus may be rotated at speeds much higher than those possible using horizontally disposed vessels means that a more efficient mixing of the vessel contents may be achieved. It has, however, been found that this mixing may be further improved by mounting the plates at an angle of at least 5° from the horizontal producing a screw effect within the vessel.

Accordingly, in a preferred embodiment the present invention also provides an apparatus for use in the process which comprises a vertically disposed cylindrical vessel closed by top and bottom plates, a plurality of inlets in the top plate communicating with the interior of the vessel and at least one outlet from the bottom plate, a stack of parallel spaced apart discs in the vessel, which discs are fixedly mounted with respect to an axially arranged rotatable shaft and are inclined at an angle of at least 5° from the horizontal and means for rotating the shaft within the vessel, and means arranged externally of the vessel for pumping the vessel contents from the bottom to the top of the vessel.

The degree of mixing within the vessel may be further improved by the adoption of additional agitation, singly or in combination. Thus, one or more impellers, which may take the form of vaned discs may be included in the disc stack.

The efficient mixing of the vessel contents according to the present invention ensures that a homogeneous system is achieved and maintained within the vessel. This efficient mixing results in rapid and complete distribution of constituents added to the vessel contents and ensures that continuous and reliable measurements of the composition and other conditions of the growth medium may be easily taken, as a result accurate process control by full instrumentation is made possible. The speed of and degree of mixing within the vessel is dependent on a combination of speed of rotation of the disc stack and the provision of auxiliary pumping means. Mixing may also further be improved by the angling of the discs from the horizontal.

The influence and inter-relationship of speed of rotation of the stack of discs and the degree of auxiliary pumping of the vessel contents may be demonstrated by injecting into the centre top of a 5 liter vessel a quantity of dye, rotating the disc stack, effecting auxiliary pumping and determining the time taken for 95% dispersion of the dye throughout the vessel contents.

The following results were obtained using a 5 liter vessel equipped with a stack of horizontally disposed plates.

| RPM | Time for 95% dispersion of dye (min). | | | | | | | | |
|---|---|---|---|---|---|---|---|---|---|
| | 0 | 3 | 6 | 11 | 17 | 30 | 40 | 50 | 60 |
| Pump Rate ml/min. | | | | | | | | | |
| 0 | — | — | — | — | 38 | 23 | 13 | 13 | 9 |
| 300 | 30+ | 30 | 23 | 9 | 11 | 9 | 7 | 8 | 7 |
| 760 | 30+ | 23 | 16 | 5 | 4 | 5 | — | — | — |
| 1060 | — | 20 | 10 | 7 | 3 | 3 | — | — | — |

(— = not determined)

The angling of the plates in the stack further contributes to efficient mixing, but, as a further important advantage, facilitates the draining of the vessel contents on emptying. Normally medium tends to be held between the plates by capillary action, but it has been found that when the plates are angled from the horizontal and the stack rotated draining efficiency is improved. The following results illustrate this principle.

| Angle from Vertical | Liquid retained (% of original) |
|---|---|
| 0° | 50 |
| 10° | 6 |
| 15° | 2 |
| 20° | 0.6 |

The possibility of using high rotational speeds with the present apparatus greatly simplifies the procedures used for harvesting cells grown in the vessel which comprise drawing the medium from the vessel and replacing it with a medium containing an enzyme capable of releasing the cells from the plates and rotating the stack of plates at high speed so that the cells are spun off into the medium which is then removed from the vessel through the outlet.

In addition merely to the growing of animal cells, the process and apparatus according to the present invention are ideally suited to the production of metabolites produced from the grown cells as a result of the introduction into the vessel of an inducer for the desired metabolite. The process and apparatus are particularly suited for such purposes because of the ability to create and maintain a homogeneous system within the vessel and to achieve rapid and complete mixing of added constituents. One example of such a process is the production of interferon and an example of the process using an apparatus according to the invention is as follows—

EXAMPLE 1

A sterile 5 liter vessel containing 100 stainless steel plates was charged with 5 liters of RPMI 1640 culture medium containing 10% v/v calf serum and an inoculum of $10^5$ cells/ml. The cell line used was the human diploid fibroblast strain 17/1. After stationary overnight incubation at 37° C. the plates were rotated at 40 rpm for 136 hours. At this stage 50% of the glucose in the culture medium had been consumed and roux flask cultures grown in parallel had become confluent and had also utilized 50% of the glucose in the culture medium. At 136 hours the medium was removed and replaced by 5 liters of RPMI 1640 containing a priming dose of fibroblast interferon. After overnight incubation interferon-inducing reagents were added. Poly IC and cycloheximide were added to a final concentration of 30 $\mu$g/ml and 5 $\mu$g/ml, respectively. Five hours after addition of these reagents, Actinomycin D (1 $\mu$g/ml) was added. After a further two hours, the culture medium was drained from the vessel and 5 liters of phosphate-buffered saline (PBS) was added. This buffer was drained off and two further BPS washes were carried out. 5 Liters of RPMI 1640 was transferred to the vessel. After a further 16 hours incubation, the culture supernatant containing interferon was harvested. The plates were rotated at 40 rpm throughout growth, interferon induction and production. The supernatant was assayed and found to contain 6000 units interferon/ml.

Figure 2:
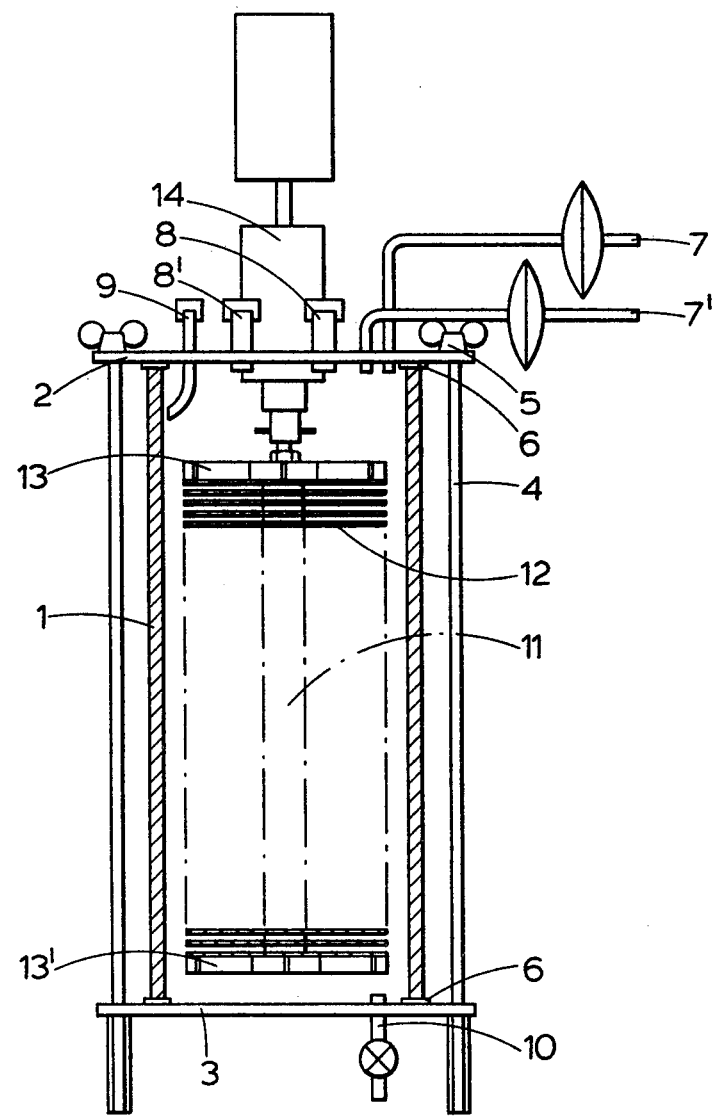

One embodiment of an apparatus for use in the process according to the present invention is illustrated in FIG. 2 of the accompanying drawing. Referring to the drawing, a cylindrical glass vessel 1 is provided with a top plate 2 and a bottom plate 3 clamped together in liquid-tight manner by rods 4 and wing nuts 5 and sealed by top and bottom silicone rubber gaskets 6. The top plate 2 is provided with five inlets: 7 and 7' for the admission of gas, 8 and 8' for the addition of reagents and 9 for the addition of medium. An outlet 10 is provided in bottom plate 3. Positioned axially within the vessel is axial shaft 11 to which are fixed a plurality of stainless steel discs 12. Also fixed to the shaft are top and bottom impellers 13 and 13'. Drive means 14 for the shaft are provided external of the vessel.

Figure 3:
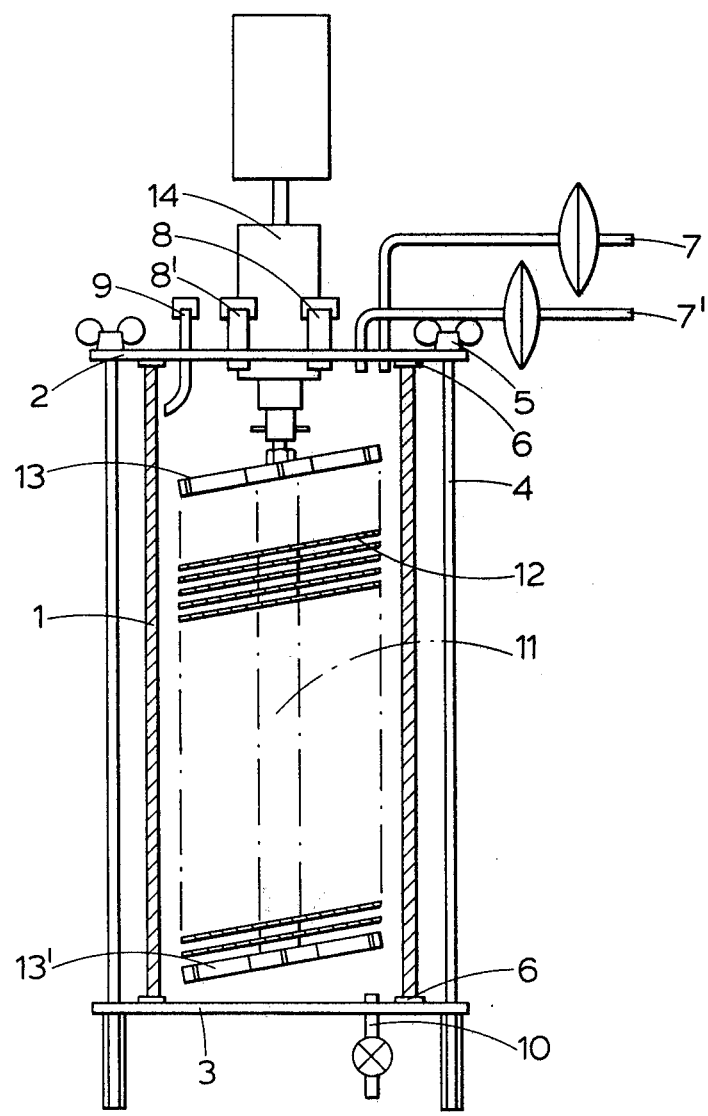

An external pumping loop (not shown) is provided for circulating the vessel contents from bottom to top. A prepared apparatus according to the present invention is shown in FIG. 3 of the accompanying drawings.

The apparatus illustrated is identical to that shown in FIG. 2, except that the plates 12 are inclined at an angle of 15° from the horizontal.

In use, the apparatus is first autoclaved and thereafter the vessel is substantially filled through inlet 9 with a suspension of the desired cells in an appropriate growth medium. Gasification of the contents of the vessel is commenced by blowing a mixture of 5% $CO_2$ and 95% air in through inlets 7 and 7'. Gasification is continued throughout the process. After filling the apparatus is allowed to stand overnight for the cells to attach to the stationary discs. After attachment, the stack of discs is rotated at a speed of from 30 to 40 rpm for from 5 to 7 days during which period the growth medium may or may not be changed depending on the growth rate of the cells. Throughout the whole process the apparatus and its contents are maintained at a controlled temperature, usually 37° C.

At the end of the period of rotation, an optimum colony of growing cells will be established and thereafter the procedure adopted will depend upon the desired purpose. If the cells are required as such, then the growth medium is removed from the vessel and replaced by buffered saline containing Trypsin to free the cells from the plates, the plates are rotated at high speed to spin the cells from the plates and the suspension of cells in saline is removed from the vessel outlet. If the cells are to be subjected to further treatment in the vessel, then the growth medium is replaced by the desired agent and rotation of the discs and controlled heating are continued until the further treatment is complete.

The present invention is further illustrated by the following Example which describes the growing of human normal diploid embryonic lung cells.

EXAMPLE 2

An apparatus as described having a vessel capacity of 6 liters and a stack of from 50 to 100 stainless steel discs was autoclaved and cooled and maintained at 37° C. The vessel was filled through inlet 9 with from 5 to 5.5 liters of a suspension of from $5 \times 10^4$ to $5 \times 10^5$ human normal diploid embryonic lung cells per ml of RPMI 1640 culture medium containing 10% v/v of calf serum. Gasification of the contents was commenced using 30 ml/min. of a mixture of 5% $CO_2$ and 95% air. The filled vessel was allowed to stand for 12 hours to allow the cells to plate onto the disc surface. Thereafter, while maintaining gasification and a temperature of 37° C., the stack of discs was rotated at from 30 to 40 rpm for from 5 to 7 days. The growth rate of the cells was measured by conventional means at intervals during this period and as and when necessary the culture medium was renewed. Any added culture medium was pre-heated to 37° C. At the end of this period, the cell growth cycle was complete. At this stage, the cells may be harvested by replacing the culture medium with buffered saline containing Trypsin, increasing the rate of revolution to spin off the cells which may be removed with the saline from outlet 10.

In addition to producing secondary metabolites using the vessel filled with medium it is also possible to achieve production when the vessel is drained of medium and the plates are maintained in a controlled water saturated gas mixture.

After release of the metabolite onto the plates, they may be harvested by refilling the vessel with a medium of choice.

This procedure provides the following advantages:

(a) If several stack vessels are used and harvested by passing medium sequentially through them it is possible to obtain the harvest in a concentrated form.

(b) The medium used for harvest may be one which does not necessarily support the growth and metabolism of cells, but which may be adapted exactly to suit following isolation steps.

(c) Avoiding the use of expensive tissue culture medium in (a) and (b) above results in major cost savings.

This embodiment of the present invention is illustrated in the following:

EXAMPLE 3

Six vessels as described above having a vessel capacity of 1 liter and a stack of 30 plates were autoclaved and cooled and maintained at 37° C. The vessels were each filled with 800 ml of a suspension of $5 \times 10^4$ human normal diploid embryo lung cells per ml of RPMI 1640 culture medium containing 10% v/v of calf serum. Gasification of the contents was commenced using 30 ml/min of a mixture of 5% $CO_2$ and 95% air. The filled vessel was allowed to stand for 12 hours to allow the cells to adhere to the disc surfaces. Thereafter, the discs were rotated at about 40 rpm for 5 days, while maintaining gasification and a temperature of 37° C. The growth rate was measured by conventional means at intervals during this period. The medium was removed and replaced by 800 ml of RPMI 1640 containing a priming dose of fibroblast interferon. After overnight incubation, interferon-inducing reagents, were added. Poly IC and cycloheximide were added to a final concentration of 30 $\mu$g/ml and 5 $\mu$g/ml respectively. 5 Hours after addition of these reagents, Actinomycin D (1 $\mu$g/ml) was added. After a further 2 hours, the culture medium was drained from the vessel and 800 ml of phosphate-buffered saline (PB5) was added. This buffer was drained and one further PBS wash carried out. 800 ml of RPMI 1640 was added sequentially from one vessel to the next and drained from the final vessel. After a further 16 hours incubation at 37° C., without gasification or rotation, 800 ml RPMI 1640 was added to each vessel to estimate the interferon produced in each vessel. (In normal use, it is preferred to add the RPMI 1640 sequentially to the vessels to harvest interferon). The mean interferon titre for the six vessels was 2512 U/ml (standard deviation=0.3).

The procedure of running the stack plates in the drained condition is also advantageous when it is necessary to treat the cells transiterily with expensive process reagents. Once again, the technique of passing such reagents sequentially through a series of stack plates will result in reagent and hence cost saving.

It will be appreciated that the use of a medium for harvesting product, while common, is not essential. If desired, product may accumulate on the plates until it is subsequently recovered.

We claim:

1. A process for growing animal cells by incubation with growth medium in a multi-plate growth apparatus which comprises substantially filling a vertically disposed cylindrical vessel with a mixture of cells and growth medium, which vessel is closed by top and bottom plates, the top plate being provided with a plurality of inlets and the bottom plate with an outlet, and the vessel is provided with a stack of parallel spaced-apart discs inclined at the angle of at least 5° from the horizontal fixedly mounted to a vertically disposed rotatable axial shaft within the vessel, while the vessel is vertically disposed allowing the cells to settle on the disc surfaces while maintaining the vessel contents at an optimum growth temperature and while infusing the vessel contents with a mixture of oxygen and carbon dioxide and thereafter while maintaining the vessel vertically disposed rotating the axial shaft at a speed of at least 5 rpm for a period of time to allow optimum growth to occur and continuously circulating the vessel contents from the bottom to the top of the vessel through an external loop.

2. A process as claimed in claim 1 in which, at the end of the growth cycle, the growth medium is replaced by a medium designed to stimulate the cells to produce a desired product and the cells are further incubated while the vessel is vertically disposed.

3. A multi-plate cell propagator apparatus which comprises a vertically disposed cylindrical vessel closed by top and bottom plates, a plurality of inlets in the top plate communicating with the interior of the vessel and at least one outlet from the bottom plate, a stack of parallel spaced-apart smooth stainless steel discs in the vessel, which discs are fixedly mounted to an axially arranged vertically disposed rotatable shaft and which are inclined at an angle of at least 5° from the horizontal, means for rotating the shaft within the vessel, and an external pumping loop means for circulating the vessel contents from the bottom to the top of the vessel.

* * * * *